(12) United States Patent
Xiao et al.

(10) Patent No.: US 8,377,341 B2
(45) Date of Patent: Feb. 19, 2013

(54) TELLURIUM (TE) PRECURSORS FOR MAKING PHASE CHANGE MEMORY MATERIALS

(75) Inventors: Manchao Xiao, San Diego, CA (US); Thomas Richard Gaffney, Carlsbad, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 927 days.

(21) Appl. No.: 12/100,824

(22) Filed: Apr. 10, 2008

(65) Prior Publication Data

US 2009/0142881 A1 Jun. 4, 2009

Related U.S. Application Data

(60) Provisional application No. 60/913,798, filed on Apr. 24, 2007.

(51) Int. Cl.
*C07C 395/00* (2006.01)

(52) U.S. Cl. .............. 252/518.1; 252/519.4; 438/102; 562/899

(58) Field of Classification Search ............ 438/102; 562/899; 252/519.4
See application file for complete search history.

(56) References Cited

U.S. PATENT DOCUMENTS

| | | | |
|---|---|---|---|
| 3,058,802 A | 10/1962 | Kulifay | |
| 3,306,701 A | 2/1967 | Thomson et al. | |
| 4,828,938 A | 5/1989 | Lichtmann et al. | |
| 4,865,822 A | 9/1989 | Tom et al. | |
| 4,946,994 A | 8/1990 | Higa | |
| 5,035,874 A | 7/1991 | Higa et al. | |
| 5,043,476 A | 8/1991 | Higa et al. | |
| 5,157,136 A | 10/1992 | Arnold et al. | |
| 5,312,983 A | 5/1994 | Brown et al. | |
| 6,447,576 B1 | 9/2002 | Otsuka et al. | |
| 6,607,829 B1 | 8/2003 | Bawendi et al. | |
| 6,682,602 B2 | 1/2004 | Vaartstra | |
| 7,045,451 B2 | 5/2006 | Shenai-Khatkhate | |
| 7,105,870 B2 | 9/2006 | Lee et al. | |
| 7,705,036 B2 * | 4/2010 | Chou et al. ............ | 514/424 |
| 7,838,329 B2 * | 11/2010 | Hunks et al. .......... | 438/102 |
| 2005/0031888 A1 | 2/2005 | Bawendi et al. | |
| 2006/0018081 A1 | 1/2006 | Lee et al. | |
| 2006/0039192 A1 | 2/2006 | Ha et al. | |
| 2006/0049447 A1 | 3/2006 | Lee et al. | |
| 2006/0061017 A1 | 3/2006 | Strouse et al. | |
| 2006/0072370 A1 | 4/2006 | Kuh et al. | |
| 2006/0092687 A1 | 5/2006 | Kuhr et al. | |
| 2006/0121391 A1 | 6/2006 | Khang et al. | |
| 2006/0172083 A1 | 8/2006 | Lee et al. | |
| 2006/0180811 A1 | 8/2006 | Lee et al. | |
| 2007/0048977 A1 | 3/2007 | Lee et al. | |
| 2007/0160760 A1 | 7/2007 | Shin et al. | |
| 2008/0035906 A1 | 2/2008 | Park et al. | |

FOREIGN PATENT DOCUMENTS

| | | |
|---|---|---|
| EP | 0140625 | 6/1988 |
| EP | 1806427 | 7/2007 |
| GB | 2148945 | 6/1985 |
| WO | 2005073976 | 8/2005 |
| WO | 2006031260 | 3/2006 |
| WO | 2007/133837 A | 11/2007 |
| WO | 2007133837 | 11/2007 |

OTHER PUBLICATIONS

K.J. Argolis, Compounds Containing a Single Carbon-Tellurium Bond, The Organic Chemistry of Tellurium, 1974, pp. 56-59.
C.W. Sink and A.B. Harvey, Vibrational Spectrum of Methanetellurol, The Journal of Chemical Physics, 1972, pp. 4434-4442, vol. 57, No. 10.
John E Drake and Raymond T. Hemmings, Studies of Silyl and Germyl Group 6 Species—Silyl and Germyl Derivatives of Methane and Benzenetellurols, Inorg. Chem, 1980, pp. 1879-1883.
K. Nagakawa, M. Osuka, K. Sasaki, Y. Aso, T. Otsubo and F. Ogura, A Novel Method for the Preparation of Ethers from Carbonyl Compounds with Benzenetellurol Catalyzed by ZnI2, Chemistry Letters, 1987, pp. 1331-1334.
B. Dabbousi, P. Bonasia and J. Arnold, (Me3Si)3SiTeH: Preparation, Characterization and Synthetic Utility of a Remarkably Stable Tellurol, J. Am. Chem. Soc., 1991, p. 3186.
R. Kirss, D. Brown, K. Higa and R. Gedridge, Jr., Pyrolysis Pathways of Symmetrical and Unsymmetrical Organotellurium (II) Compounds, Organometallics, 1991, pp. 3589-3596.
K. Hamada and H. Morishita, The Proton NMR of CH3—X—H(X=O, S, Se, Te), Japan. J. Appl. Phys., 1976, p. 748.
T.B. Rauchfuss, Acidity, hydrogen bonding and self-association in organic and organometallic compounds of selenium and tellurium, The Chemistry of Organic Selenium and Tellurium Compounds, 1987, pp. 339-347.
L. Dennis and R. Anderson, Hydrogen Telluride and the Atomic Weight of Tellurium, J. Am. Chem. Soc., 1914, p. 882-909.
Naumann, D.; "On Perfluoroalkyl Tellurium Compounds"; Phosphorous, Sulfur and Silica; 2001; vol. 171; pp. 113-133; XP009106724.
Arnold, J., et al; "Growth of II-VI Thin Films form Single-Source Precursors Based on Sterically Encumbered Sitel Ligands"; Journal of Crystal Growth; 1992; vol. 124; pp. 647-653; XP009106728.
Gedridge, R.W., et al; "New Organotellurium Precursors for the Pyrolytic and Photolytic Deposition"; Mat. Res. Soc. Symp. Proc.; 1989; vol. 131; pp. 69-73; XP009106734.

* cited by examiner

*Primary Examiner* — Mark Kopec
*Assistant Examiner* — Haidung Nguyen
(74) *Attorney, Agent, or Firm* — Lina Yang

(57) ABSTRACT

Tellurium (Te)-containing precursors, Te containing chalcogenide phase change materials are disclosed in the specification. A method of making Te containing chalcogenide phase change materials using ALD, CVD or cyclic CVD process is also disclosed in the specification in which at least one of the disclosed tellurium (Te)-containing precursors is introduced to the process.

2 Claims, No Drawings

TELLURIUM (TE) PRECURSORS FOR MAKING PHASE CHANGE MEMORY MATERIALS

CROSS REFERENCE TO RELATED APPLICATIONS

This application claims the benefit of priority under 35 U.S.C. §119(e) to earlier filed U.S. patent application Ser. No. 60/913,798, filed on Apr. 24, 2007.

BACKGROUND OF THE INVENTION

Phase-change materials exist in a crystalline state or an amorphous state according to temperature. A phase-change material has a lower resistance and a more ordered atomic arrangement in a crystalline state than in an amorphous state. A phase-change material can be reversibly transformed from the crystalline state to the amorphous state based on an operating temperature. Such characteristics, that is, reversible phase change and different resistances of different states, are applied to newly proposed electronic devices, a new type of nonvolatile memory devices, phase-change random access memory (PRAM) devices. A resistance of a PRAM may vary based on a state (e.g., crystalline, amorphous, etc.) of a phase-change material included therein.

Various types of phase-change material can be used for memory devices, the most commonly used phase change materials are ternary composition of chalcogenides of group 14 and group 15 elements, such as germanium-antimony-tellurium compounds, commonly abbreviated as GST. The solid phases of GST can rapidly change from crystalline to amorphous or vise versa upon heating and cooling cycles. The amorphous GST has relatively higher electric resistance and the crystalline GST has relatively lower electric resistance.

Currently, Physical Vapor Deposition (PVD) processes, or spattering, are used in the manufacture of re-writable optical disks to coat a thin layer of phase change material on the plastic substrates. However, the PVD processes are not suitable for electronic devices due to film growth control and film properties. To make PRAM, Chemical Vapor Deposition (CVD), or Atomic Layer Deposition (ALD) techniques are used to deposit a thin film of GST on the substrate of silicon. The development of phase-change memory devices raises the need for ALD/CVD processes with proper precursors for low temperature deposition.

BRIEF SUMMARY OF THE INVENTION

The present invention satisfies the need by providing the tellurium-containing compounds as Te precursors for deposition of ternary germanium-antimony-tellurium films by low temperature ALD, CVD or cyclic CVD processes.

A Te containing composition is disclosed in the specification. The Te containing composition comprises deuterated an organotellurol having a general structure of:

R—Te-D wherein R is selected from the group consisting of an alkyl group or an alkenyl group having 1 to 10 carbons in linear, branched, or cyclic form; an aromatic group having $C_{6-12}$; a dialkylamino group; an organosilyl group; and an organogermyl.

A Te containing chalcogenide phase change material is disclosed in the specification. The Te containing chalcogenide phase change material is prepared by depositing a Te precursor selected from the group consisting of (a) an organotellurol having a general structure of:

R—Te—R' wherein R is selected from the group consisting of an alkyl group or an alkenyl group having 1 to 10 carbons in linear, branched, or cyclic form; an aromatic group having $C_{6-12}$; a dialkylamino group; an organosilyl group; and an organogermyl; and R' is selected from the group consisting of hydrogen and deuterium;

(b) a composition having a general structure of:

$R''_2Te$ wherein R" is selected from the group consisting of hydrogen and deuterium; and (c) tellurium hexafluoride.

A process of depositing Te containing chalcogenide phase change material on a substrate is also disclosed in the specification. The process comprises steps of:

depositing a Te precursor comprising a Te-containing composition selected from the group of:

(a) an organotellurol having general structure of:

R—Te—R' wherein R is selected from the group consisting of an alkyl group or an alkenyl group having 1 to 10 carbons in linear, branched, or cyclic form; an aromatic group having $C_{6-12}$; a dialkylamino group; an organosilyl group; and an organogermyl; and R' is selected from the group consisting of hydrogen and deuterium;

(b) a general structure of:

$R''_2Te$ wherein R" is selected from the group consisting of hydrogen and deuterium; and (c) tellurium hexafluoride reacting with ammonia;

depositing a Ge precursor comprising aminogermanes having a general structure of:

$(R^1R^2N)_4Ge$ wherein $R^1$ and $R^2$ are alkyl groups having 1 to 10 carbons in linear, branched, or cyclic form; and depositing a Sb precursor comprising aminostibanes having a general structure of:

$(R^1R^2N)_3Sb$ wherein $R^1$ and $R^2$ are alkyl groups having 1 to 10 carbons in linear, branched, or cyclic form.

The three deposition steps in the process can be carried out sequentially in any order or concurrently. Or, any two of three deposition steps can be carried out concurrently. The process is carried out at 100-400° C. by ALD, CVD, or cyclic CVD processes.

DETAILED DESCRIPTION OF THE INVENTION

The present invention is related to selected tellurium compounds as Te precursors, and using the selected tellurium compounds along with aminogemanium and aminoantimony compounds, in a low temperature process to produce ternary germanium-antimony-tellurium films via ALD, CVD or cyclic CVD processes.

In one embodiment of the present invention, the Te precursor for low temperature deposition process comprises hydrogen telluride ($H_2Te$). Aminometal compounds are reactive toward hydrolysis. Hydrogen chalcogenides are all more acidic than water. The reactions of aminogermanes and aminoantimony with hydrogen telluride form metal tellurides at low temperature (<250° C.). The deposition of tetrakis(dimethylamino)germane, (Me₂N)₄Ge, and tris(dimethylamino) antimony, (Me₂N)₃Sb, followed by the treatment with hydrogen telluride is a suitable approach for ALD or CVD processes of making GST films for phase change memory applications. Hydrogen telluride is a gaseous compound with a boiling point of −4° C. It is unstable above 0° C., and it decomposes into elemental tellurium and hydrogen. To overcome this problem, hydrogen telluride can be produced by in situ generation, and immediately introduced into the reaction chamber.

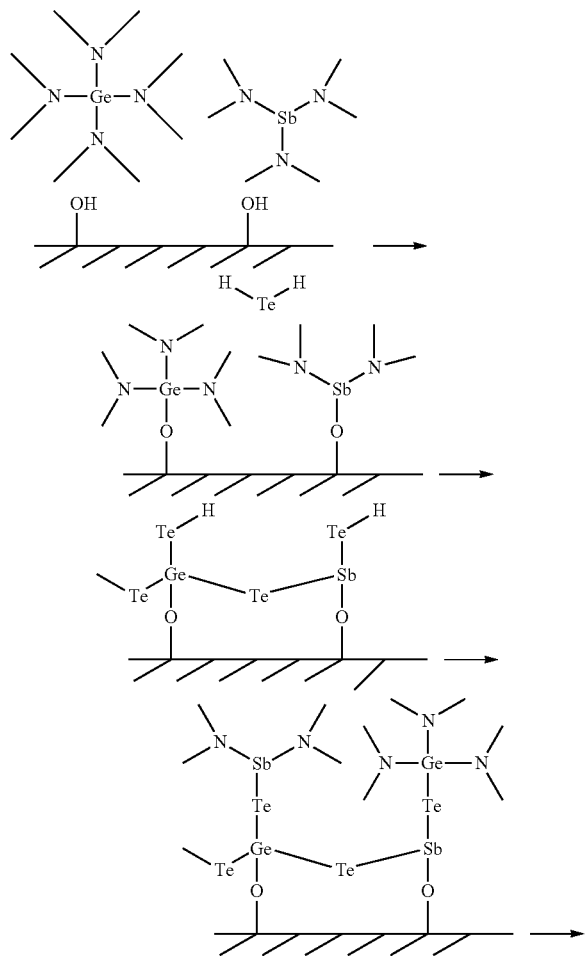

In another embodiment of the present invention, the Te precursor comprises deuterium telluride (D₂Te). Deuterium is the heavier isotope of hydrogen (where the nucleus has an added neutron). Deuterium telluride has improved thermal stability, compared with the corresponding regular hydrogen telluride.

As more thermally stable tellurium compounds, organotellurols and deuterated organotellurols are disclosed as more suitable tellurium precursors for ternary germanium-antimony-tellurium film depositions.

In another embodiment of the present invention, the Te precursor for low temperature deposition process comprises organotellurols. Organotellurols have acidic Te—H bonds, which are highly reactive to the Ge—N and Sb—N bonds in the corresponding aminometal compounds. Te—Ge and Te—Sb bonds form at relatively low temperature, with the volatile amines as leaving compounds. The reaction is illustrated in the following scheme:

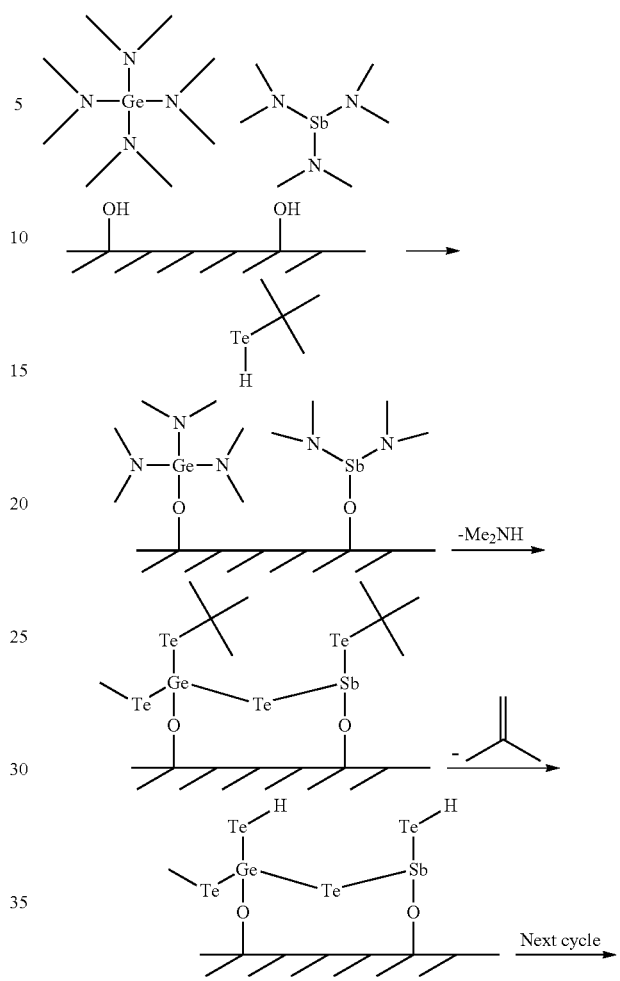

The Te precursor comprising organotellurols has a general formula of $$R-Te-R'$$

where R is an alkyl group or alkenyl group having 1 to 10 carbons in linear, branched, or cyclic form; or an aromatic group having $C_{6-12}$, such as phenyl; or a dialkylamino group; or an organosilyl group; or an organogermyl group; R' is hydrogen or deuterium.

Alkyl tellurols are the preferred tellurium precursors. They are volatile liquids and can be delivered by vapor draw or direct liquid injection methods. T-Butyltellurol has a weak Te—C bond with a bond energy of 26 kcal/mole. The t-butyl group can be cleaved at relatively low temperature. This helps to reduce the carbon content in the resulting GST films.

Deuterated organotellurols have improved thermal stability, compared with the corresponding regular organotellurols, resulting in longer shelf life and wider process windows. Due to the primary kinetic isotope effect, Te-D bond is more stable than Te—H bond. Therefore, deuterated organotellurols have less tendency to decompose during storage and delivery, while maintaining the similar chemical reactivity to form tellurides with germanium and antimony.

Examples of Te precursors comprising deuterated organotellurols are N-Butyltellurol-D and T-Butyltellurol-D, where "D" is deuterium.

In another embodiment of the present invention, the Te precursor comprises tetrakis(dialkylamino)tellurium, wherein, the alkyl group is independently selected from the group consisting of methyl, ethyl, propyl, isopropyl, butyl, and t-butyl.

The Te precursor comprising tetrakis(dimethylamino)tellurium can be mixed with tetrakis(dimethylamino)germanium (Me$_2$N)$_4$Ge and tris(dimethylamino)stilbane to form uniform solutions in desired molar ratios. Such a solution is introduced to the deposition chamber by direct liquid injection methods. The chemicals are deposited on the surface of a heated substrate. The following reduction reaction by hydrogen or hydrogen plasma removes the amino groups and forms a GST layer with the proper elemental ratio. These steps form a cycle for ALD or cyclic CVD process.

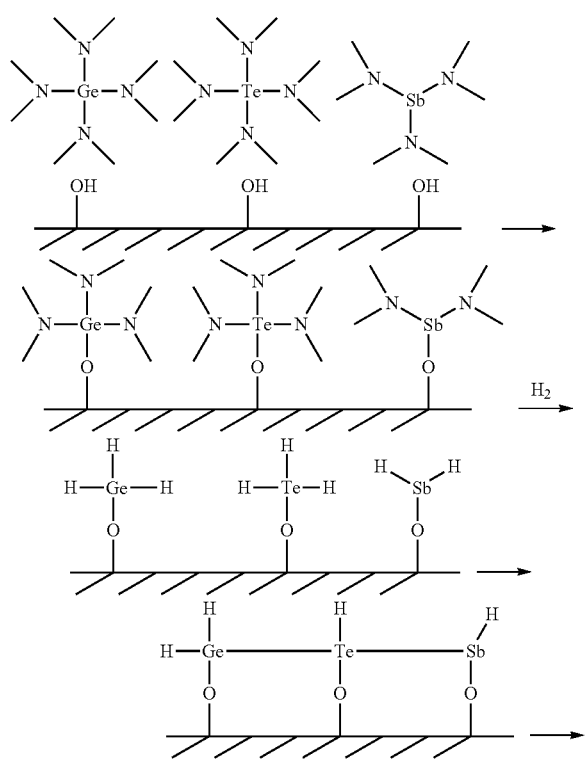

In yet another embodiment of the present invention, the Te precursor comprises tellurium hexafluoride. Tellurium hexafluoride TeF$_6$ is a colorless gas with a boiling point of −38° C. Unlike the sulfur analog, tellurium hexafluoride is not chemically inert. This can be attributed to the greater availability of the d orbital and perhaps the availability of the f orbital, which neither sulfur nor selenium has access to.

In another embodiment of the present invention, Te containing chalcogenide phase change material is prepared by depositing a Te precursor selected from any of previous disclosed embodiments, via any known deposition method, such as by ALD, CVD, or cyclic CVD processes.

In yet another embodiment of the present invention, the process of making a Te-containing chalcogenide phase change material, may employ depositing a Te precursor from any of previous disclosed embodiments with a Ge precursor and a Sb precursor via any known deposition method, such as by ALD, CVD, or cyclic CVD processes.

Examples of a Ge precursor and a Sb precursor are aminogermanes and aminostibanes having the general structures of:

(R$^1$R$^2$N)$_4$Ge and (R$^1$R$^2$N)$_3$Sb

Where R$^1$ and R$^2$ are independently alkyl groups having 1 to 10 carbons in chain, branched, or cyclic form.

For example, as a tellurium precursor, tellurium hexafluoride can react with ammonia in a deposition chamber to form aminotellurium, which may subsequently react with aminogermanes and aminostibanes, followed by hydrogen reduction to generate GST films on a substrate.

TeF$_6$+NH$_3$→[Te(NH$_2$)$_n$]+NH$_4$F

In the process for making the GST thin films, three precursors can be deposited sequentially. Any one of the three precursors, such as the Ge precursor is deposited on the surface of a heated substrate that has a suitable temperature for the chemical reaction. After a purging/cleaning step, such as by flowing inert gas, the second precursor, such as the Sb precursor is deposited on the surface of the substrate having Ge thin layer. After another purging/cleaning step, the last precursor, such as the Te precursor is deposited on the substrate having Ge and Sb thin layer. Any one of the three precursors can be the first or the second or the third precursors for the process. For the purpose of the present invention, depositing on a substrate includes not only deposition directly on the substrate itself, but also deposition on one at the other of the three reactants already deposited on the substrate.

Alternatively, the deposition process can deposit any two of the three precursors concurrently, or all three precursors concurrently.

In addition, the deposition process can be repeated to make multi-layer films.

The film deposition can be carried out at 100-400° C.

WORKING EXAMPLES

In preparing the Te precursor for lower temperature deposition, any of the various known methods, may be employed. Among the known methods, a method of preparing the Te precursor according to embodiments of the examples of the present invention is described as follows.

Example I

Synthesis of N-Butyltellurol-D 6.4 g (0.05 mol) 200 mesh tellurium powder, 100 ml diethyl ether, and 20 ml 2.5 M n-butyllithium in hexane were added to a 250 ml flask. At 0° C., the mixture was stirred for 8 hours. All black powder of tellurium disappeared and a muddy color precipitate was formed. To this mixture, 5.4 g (0.05 mol) trimethylchlorosilane was added. The mixture was allowed to warm up to room temperature. After stirring for 2 hours, 2.0 g (0.06 mol) deuterated methanol (MeOD) was added slowly. After stir for 1 hour, the mixture was filtered under inert atmosphere. The solvent and by product methoxytrimethylsilane were removed by distillation. A vacuum distillation gave N-Butyltellurol-D. The boiling point is 85° C./100 mmHg.

Example II

Synthesis of T-Butyltellurol-D 12.8 g (0.10 mol) 200 mesh tellurium powder, 250 ml diethyl ether, and 50 ml 2.0 M t-butylmagnesium chloride solution in diethyl ether were added to a 500 ml flask. At room temperature, the mixture was stirred for 24 hours. All black powder of tellurium disappeared and a light gray color precipitate was formed. The mixture was cooled to −50° C. with a dry ice bath. To this mixture, 10.0 g (0.21 mol) deuterated ethanol (EtOD) was added slowly. The mixture was allowed to warm up to room temperature. After stirring for 2 hours, the mixture was filtered under inert atmosphere. The solvent ether was removed by distillation. A vacuum distillation gave T-Butyltellurol-D. The boiling point is 65° C./100 mmHg.

The embodiments of this invention listed above, including the working example, are exemplary of numerous embodiments that may be made of this invention. It is contemplated that numerous other configurations of the process may be used, and the materials used in the process may be elected from numerous materials other than those specifically disclosed.

The invention claimed is:

1. A Te containing composition comprising deuterated organotellurol having a general structure of:

R—Te-D wherein R is selected from the group consisting of N-butyl, T-Butyl and an alkenyl group having 1 to 10 carbons in linear, branched, or cyclic form; an aromatic group having $C_6$-$C_{12}$; a dialkylamino group; an organosilyl group; and an organogermyl, and D is deuterium.

2. The Te containing composition of claim 1 selected from the group consisting of N-Butyltellurol-D and T-Butyltellurol-D.

* * * * *